United States Patent
Buelow et al.

(10) Patent No.: US 12,109,063 B2
(45) Date of Patent: Oct. 8, 2024

(54) APPARATUS CONFIGURED TO CREATE A SCAN PROTOCOL WITH AN INTERACTIVE TOOL AND/OR EVALUATE ADHERENCE TO THE PROTOCOL

(71) Applicant: KONINKLIJKE PHILIPS N.V., Eindhoven (NL)

(72) Inventors: Thomas Buelow, Grosshansdorf (DE); Cristian Lorenz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 872 days.

(21) Appl. No.: 16/972,869

(22) PCT Filed: May 30, 2019

(86) PCT No.: PCT/EP2019/064128
§ 371 (c)(1),
(2) Date: Dec. 7, 2020

(87) PCT Pub. No.: WO2019/233882
PCT Pub. Date: Dec. 12, 2019

(65) Prior Publication Data
US 2021/0244376 A1    Aug. 12, 2021

Related U.S. Application Data

(60) Provisional application No. 62/682,189, filed on Jun. 8, 2018.

(51) Int. Cl.
*A61B 6/00* (2024.01)
*A61B 6/03* (2006.01)
*A61B 6/46* (2024.01)

(52) U.S. Cl.
CPC .............. *A61B 6/545* (2013.01); *A61B 6/032* (2013.01); *A61B 6/463* (2013.01); *A61B 6/465* (2013.01)

(58) Field of Classification Search
CPC ......... A61B 6/545; A61B 6/032; A61B 6/463; A61B 6/465; A61B 6/488; A61B 6/469;
(Continued)

(56) References Cited

U.S. PATENT DOCUMENTS

2006/0224348 A1  10/2006 Shankarappa et al.
2012/0089377 A1   4/2012 Erhard et al.
(Continued)

FOREIGN PATENT DOCUMENTS

DE   102012201798 A1   8/2013
JP     2015213749 A    12/2015

OTHER PUBLICATIONS

International Search Report and Written Opinion for International Application No. PCT/EP2019/064128, filed May 30, 2019, 20 pages.

*Primary Examiner* — Joel Lamprecht (57) ABSTRACT

An apparatus including a memory (128), a display (122), and a processor (126). The memory is configured to store a protocol definition module (132). The processor is configured to execute the protocol definition module, which causes the processor to display, via the display, an interactive graphical tool (202) that includes a digital representation of an anatomical model with an interactively generated scan field of view superimposed thereover to create a standard scan protocol for execution by an imaging system, wherein the scan field of view identifies anatomy of the subject to scan for the scan protocol.

14 Claims, 4 Drawing Sheets

(58) Field of Classification Search
CPC .............................. A61B 6/544; A61B 6/5229; G06V 2201/031; G16H 30/20; G16H 20/40; G16H 40/63
See application file for complete search history.

(56) References Cited

U.S. PATENT DOCUMENTS

| | | |
|---|---|---|
| 2012/0121152 A1 | 5/2012 | Lu et al. |
| 2013/0083894 A1 | 4/2013 | Niebler et al. |
| 2015/0104092 A1 | 4/2015 | Flohr et al. |
| 2015/0297157 A1* | 10/2015 | Mukumoto ............ A61B 6/465 378/15 |
| 2016/0078687 A1 | 3/2016 | Van Bree et al. |
| 2016/0213329 A1 | 7/2016 | Dirkes |
| 2016/0367169 A1 | 12/2016 | Hardie et al. |
| 2017/0024911 A1* | 1/2017 | Grodzki ................ A61B 5/055 |
| 2017/0364644 A1* | 12/2017 | Johnson ................ G16H 80/00 |
| 2020/0054398 A1* | 2/2020 | Kovtun ................ G16H 40/63 |

* cited by examiner

APPARATUS CONFIGURED TO CREATE A SCAN PROTOCOL WITH AN INTERACTIVE TOOL AND/OR EVALUATE ADHERENCE TO THE PROTOCOL

RELATED APPLICATIONS

This application is the U.S. National Phase application under 35 U.S.C. § 371 of International Application No. PCT/EP2019/064128, filed on May 30, 2019, which claims priority to and the benefit of Provisional Application No. 62/682,189, filed Jun. 8, 2018, which are incorporated by reference in their entireties.

FIELD OF THE INVENTION

The following generally relates to an apparatus configured to create a scan protocol with an interactive tool and/or evaluate adherence of a scan based on the scan protocol to the scan protocol, and is described with particular application to computed tomography (CT) imaging, but it also amenable to other imaging modalities such as magnetic resonance imaging (MRI), etc.

BACKGROUND OF THE INVENTION

A computed tomography (CT) scanner includes an x-ray tube that emits radiation. The emitted radiation traverses an examination region with a subject or object located within and is detected by a detector array opposite from the x-ray tube. The detector array detects the radiation traversing the examination region and the subject located therein and generates projection data. A reconstructor processes the projection data and reconstructs a projection image and/or volumetric image data of the subject or object.

Generally, a pre-scan is first performed to generate a radiographic like projection image of a portion of the subject or object. The projection image is used along with a scan protocol for the clinical reason to create a scan plan for a volume scan of the subject or object. This includes, e.g., defining a field of view (i.e. a start scan position, a scan extent or a stop scan position), etc. to scan anatomy of interest. The volume scan of the subject or object is then performed with the scan plan to generate the volumetric image data of the anatomy of interest.

Often times scan protocols are defined at an institution level to be specific to a radiologist and/or a healthcare facility. As such, field of views for a same clinical reason may differ between institutions. Furthermore, the scan protocols have often been descriptive in nature, e.g., radiologists explaining how they would like imaging examinations to be performed to technicians setting up and performing the scans. Hence, it may be difficult to assure adherence of scans to the scan protocols.

SUMMARY OF THE INVENTION

Aspects described herein address the above-referenced problems and others.

In one aspect, an apparatus includes a memory, an input device, a display, and a processor. The memory is configured to store a protocol definition module. The processor is configured to execute the protocol definition module, which causes the processor to display, via the display, an interactive graphical tool that includes a digital representation of an anatomical model with an interactively generated scan field of view superimposed thereover to create a standard scan protocol for execution by an imaging system, wherein the scan field of view identifies anatomy of the subject to scan for the scan protocol.

In another aspect, an apparatus includes a memory and a processor. The memory is configured to store a protocol adherence module. The processor is configured to execute the protocol adherence module, which causes the processor to analyze a plurality of sets of volumetric image data generated by one or more imaging system programmed with a scan protocol for a plurality of different scans to determine whether the sets of volumetric image data adheres to the scan protocol.

In another aspect, a computer readable medium is encoded with computer executable instructions. The instructions, when executed by a processor, cause the processor to: analyze volumetric image data generated by an imaging system executing a scan plan created from the scan protocol to determine whether the volumetric image data adheres to the scan protocol, and visually present, in a display, information indicating whether the volumetric image data adheres with the scan protocol.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following generally describes an interactive tool for defining a scan protocol including a scan field of view of interest and/or evaluating volume scans that are based on the scan protocols for adherence with the scan protocols. For sake of brevity and explanatory purposes, the following is described with particular application to CT. However, the following is also amenable to MRI and/or other imaging modalities.

Figure 1:
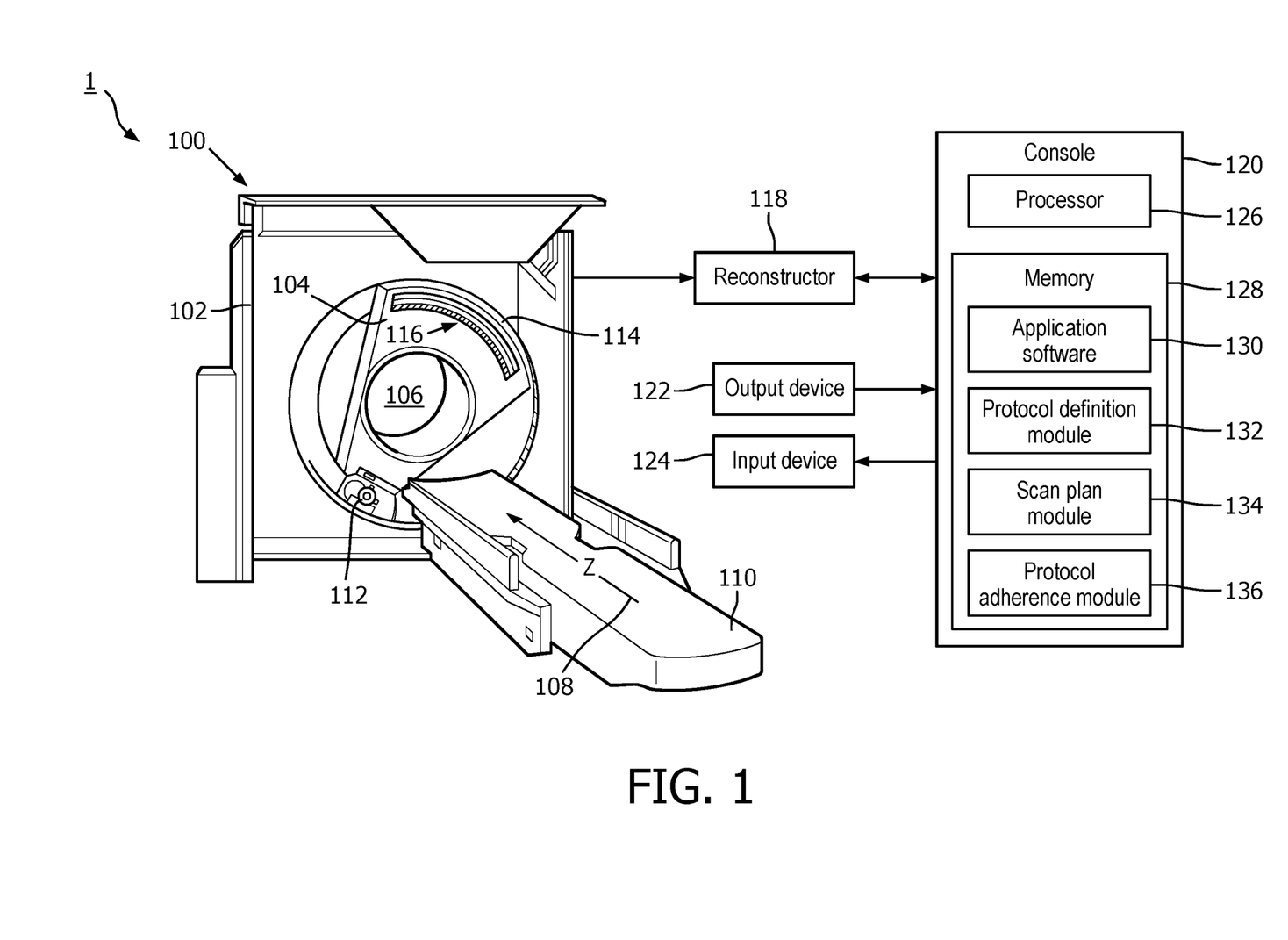
FIG. 1 schematically illustrates an example system with an imaging system and a computing apparatus with at least a protocol definition module and a protocol adherence module.

FIG. 1 schematically illustrates an example system 1 with an example imaging system 100 such as a computed tomography (CT) system. The imaging system 100 includes a stationary gantry 102 and a rotating gantry 104, which is rotatably supported by the stationary gantry 102. The rotating gantry 104 rotates around an examination region 106 about a longitudinal or z-axis 108. A subject support 110 is configured to support an object or subject in the examination region 106 so as to guide the subject or object with respect to the examination region 106 for loading, scanning, and/or unloading the subject or object.

An X-ray radiation source 112, such as an x-ray tube, is supported by the rotating gantry 104 and generates and emits X-ray radiation that traverses the examination region 106. A radiation sensitive detector array 114 includes one or more rows 116 of detector elements, each of the rows 116 extending along a direction transverse to the z-axis 108 and arranged parallel to the other rows other along the z-axis 108. The radiation sensitive detector array 114 detects X-ray radiation traversing the examination region 106 and generates an electrical signal (projection data) indicative thereof. A reconstructor 118 reconstructs the projection data and generates a projection (2-D) image and/or volumetric (3-D) image data, depending on the type of scan.

The system 1 further includes a computer that serves as an operator console 120 and that includes a human readable output device 122 such as a display, an input device 124 such as a keyboard, mouse, etc., a processor 126 (e.g., a microprocessor, a central processing unit (CPU), etc.), and computer readable storage medium (memory) 128, which includes non-transitory medium (hardware memory) and excludes transitory medium (signals, carrier waves, and the like). Application software 130 resident on the operator console 120, when executed by the processor 126, allows an operator to control an operation of the imaging system 100 such as selecting a type of scan (e.g., a projection scan or a volume scan), selecting an imaging protocol, etc. through a graphical or other user interface.

A projection scan (also referred to as a pre, scout, pilot, surview, etc.) is performed to generate a pre-scan projection image. This pre-scan projection image is used to create a scan plan for a volume scan, which is then performed to generate the volumetric image data. In one instance, the projection scan is performed with the rotating gantry 104 and hence the X-ray radiation source 112 at a static position, X-rays turned on, and the subject support moving the patient through the examination region 106 from a preset start position over a preset distance or to a preset end position. Alternatively, the rotating gantry 104 and hence the X-ray radiation source 112 rotates, and X-rays are emitted only a predetermined angular location(s) (e.g., 0 degrees and/or 90 degrees). The resulting projection image is similar to an X-ray radiograph.

A volume scan is performed based on the created scan plan with the rotating gantry 104 and hence the X-ray radiation source 112 rotating around the examination region 106 and X-rays turned on continuously or turned on intermittently (e.g., using an X-ray tube grid switch, a radiation attenuating filter, etc. to control the duty cycle). For an axial scan, the subject support supports the patient at a static position. For a spiral/helical scan, the subject support moves the patient through the examination region 106 from the start position to the end position in the imaging plan. The resulting volumetric image data is created from cross-sectional slices through the patient. An axial, a sagittal, a coronal, and/or an oblique 2-D image and/or a 3-D image can be derived from the volumetric image data.

The illustrated computer readable storage medium 128 further includes at least a protocol definition module 132, a scan plan module 134, and a protocol adherence module 136. The modules 132, 134 and 136 include computer executable instructions, which when executed by the processor 126, cause the processor to perform the functions of the modules 132, 134 and 136 described herein. As described in greater detail below, in one instance the protocol definition module 132 provides an interactive graphical tool with a digital representation of an anatomical model that allows an authorized user to define a scan protocol, the scan plan module 134 employs the defined scan protocol with a pre-scan projection image to create a scan plan for a volume scan, and the protocol adherence module 136 determines whether a completed scan adhered to the scan protocol.

Figure 2:
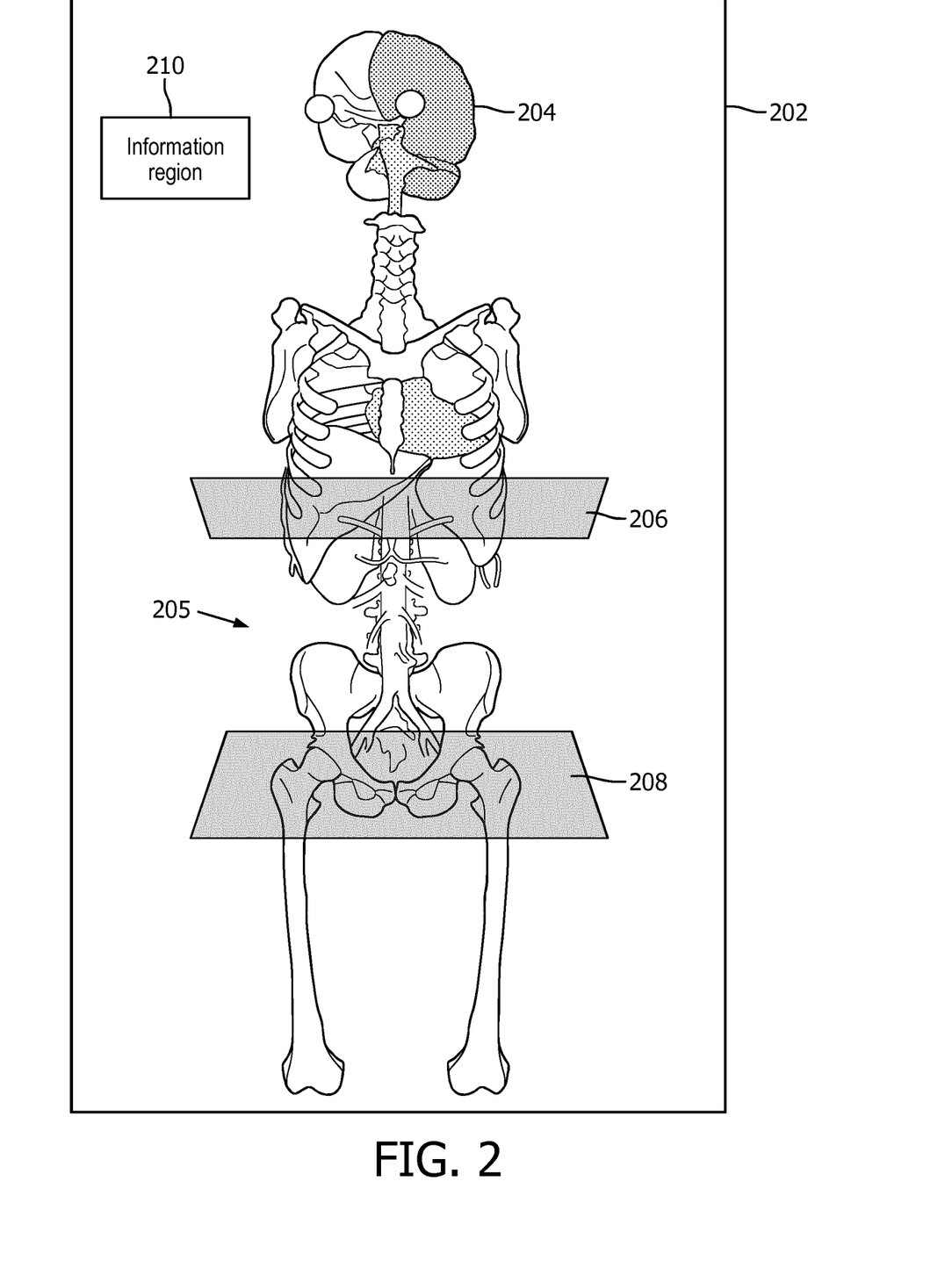
FIG. 2 schematically illustrates an interactive graphical tool of the protocol definition module to define scan protocols that includes an anatomical surface model.

Although shown as stored in the computer readable storage medium 128 of the console 120, in a variation one or more of the protocol definition module 132, the scan plan module 134, and the protocol adherence module 136 is stored in memory external to and remote from the console 120, e.g., in memory of another console of another imaging system, in memory of a computer workstation, in memory accessible through a network (e.g., "cloud" based or other storage), etc. In one instance, the one or more of the module 132, 134 and 136 is executed by the processor 126. In another instance, at least one of the modules 132, 134 and 136 is executed by one or more processors external to and remote from the console 120, e.g., in a console of the other imaging system, the computer workstation, in the "cloud," etc. FIG. 2 shows an example of an interactive graphical tool 202 of the protocol definition module 132 for creating a scan protocol. The interactive graphical tool 202 is visually presented via a display device of the output device 122 and/or otherwise.

The interactive graphical tool 202 visually presents a surface model 204 of a portion of an anatomical model. One approach to creating the surface model 204 includes overlaying a 2-D triangular mesh on top of an image and then building a corresponding 3-D mesh by placing vertices of the triangles in 3-D space according to the values found in a depth map. Other surface models are also contemplated herein. Additionally, or alternatively, the interactive graphical tool 202 visually presents an anatomical atlas, which is an image in which each voxel has a probability representing particular anatomical tissue. The interactive graphical tool 202 can toggle between different types of digital representations and/or concurrently display them. The digital representation can be constructed for an average subject and/or specific to the patient to be scanned.

An example of a suitable surface model is described in Weese, et al., "Shape constrained deformable models for 3D medical image segmentation," In: Biennial International Conference on Information Processing in Medical Imaging, Springer, Berlin, Heidelberg, 2001. S. 380-387. An example of a suitable probabilistic atlas is discussed in Franz, et al., "Annotation-free probabilistic atlas learning for robust anatomy detection in CT images," SPIE Medical Imaging: Image Processing, volume 9413, 941338, 2015. An example approach to build the context of the human anatomy is discussed in Pflesser, et al., "Exploring the visible human's inner organs with the VOXEL-MAN 3D navigator," Studies in health technology and informatics, 2001, S. 379-385. Other approaches are contemplated herein.

In one instance, the portion of the subject in the surface model 204 is the same (e.g., the entire body even for a head scan) regardless of the anatomy of interest. In another instance, the portion of the subject in the surface model 204 is specific to the anatomy of interest (e.g., only the head for a head scan and not the entire body). In the latter instance, the user first identifies the anatomy (e.g., head), and the processor 126 automatically retrieves and renders a surface model (from a plurality of surface models) with the identified anatomy. Alternatively, the user selects a surface model from a library of available surface models. Furthermore, the surface model 204 can be specific to the tissue of interest, e.g., vascular, soft tissue, bone, etc., and/or include landmarks associated with the tissue of interest.

In the illustrated embodiment, the surface model 204 is pre-populated with a scan field of view 205, which is defined by a space between user defined delimiting structures, such an upper plane 206 and a lower plane 208. In another embodiment, the scan field of view 205 is defined through a bounding box, etc. In the illustrated embodiment, the scan field of view 205 has a cube shape. In other embodiments, the scan field of view 205 has an arbitrary shape (e.g., cylindrical, etc.) and/or an oblique orientation (e.g., following the spine direction). The planes 206 and/or 208 can be standardized planes and/or predetermined planes of other users from publicly available libraries, etc. In a variation, the surface model 204 is pre-populated with three or more planes. In another variation, the surface model 204 is not pre-populated with any planes. In this instance, the interactive graphical tool 202 includes planes from which the user can select and/or drag and drop over the surface model 204. The user can adjust a geometry and/or location of the plane 206 and/208. In one instance, this includes using a graphical pointer (e.g., for a mouse input device 124) and moving a corner or side of a plane and/or the entire plane.

Additionally, or alternatively, the interactive graphical tool 202 includes an information region 210, which visually presents a description such as offsets, widths, angularization (e.g., planes tilted with respect to the longitudinal axis of the subject), slice thickness, image resolution, 2D or 3D, a specific organ (e.g., the heart), etc., used to define the scan planes 206 and 208. The information region 210 can also include other information such as a landmark and/or organ to be included and/or excluded, an external device being used for the scan, scan parameters, CT dose, etc. used to define the scan planes 206 and 208. The illustrated size, shape and/or location of the information region 210 is for explanatory purposes and is not limiting. In a variation, the information region 210 is omitted from the interactive graphical tool 202.

Examples of landmarks include a bifurcation of the aorta and branches of a vessel, a center of vertebra, a tip, end, side, etc. of an organ, and/or other features associated with locating the anatomy of interest. The planes 206 and 208 can be adjusted accordingly to ensure that any organs and/or landmarks that should be in the image are in the image and/or any organs and/or landmarks that should not be in the image are not in the image. An example of an external device is a device to position the subject. For example, the prop can be a pillow placed under the head of the subject to angle the head for diagonal planes, e.g., to avoid irradiating the eyes of the subject. In one instance, the information region 210 allows the user to adjust the information therein, e.g., through manually entering data, selecting data from a menu, etc. Generally, the pre-scan is already acquired using the prop so that the scan protocol and the pre-scan can be used to create a volume scan plan.

Scan protocols generated with the protocol definition module 132 using the interactive graphical tool 202 are stored in the memory 128 (FIG. 1) and/or other storage such as in central storage of an imaging center, a radiology information system (RIS), a hospital information system (HIS), "cloud" based storage, etc. A scan protocol in such storage can be edited using the interactive graphical tool 202 and/or otherwise. Furthermore, a scan protocol in such storage can be deleted using the interactive graphical tool 202 and/or otherwise. The scan protocols can also be shared across imaging systems, facilities within a healthcare institution, healthcare institutions, etc. The stored scan protocols, in one instance, are "standardized" protocols to be used and followed by the healthcare institution(s) when scanning subjects.

By way of non-limiting example, the scan protocol in one instance is for a scan of the abdominal aorta in the context of a scan of an abdominal aneurism. A contrasted CT scan is typically acquired to capture a shape of an aneurism and a position of the arterial branches. The branches have been used during an analysis phase when flow and pressure characteristics are calculated to estimate the rupture probability. The branches have also been used during an intervention planning phase since a typical stent is selected such that important branches are blocked. Another option includes specific outflow parts in the aortic stent. For both options, coverage of important branching arteries, such as the renal, iliac, and mesenteric arteries are crucial for successful image acquisition. The interactive graphical tool 202 can be used to create a scan protocol that adheres to these criteria.

As briefly described above, the scan plan module 134 employs the defined scan protocol with a pre-scan projection image to create a scan plan for a volume scan. In this example, this includes using segmentation, an anatomical awareness, and/or the like to estimate organ positions and extensions in the pre-scan projection image to facilitate translating the planes 206 and 208 and the information in the information region 210 to patient geometries to create the scan plan, e.g., through registration and/or other approaches to transfer the geometrical information. The user can adjust the volume scan plan as desired. The volume scan plan is then used to program the imaging system 100 and/or other imaging system to scan the patient. The volume scan plan and/or the resulting image data are also stored in memory such as the memory 128, the central storage of the imaging center, the RIS, the HIS, the "cloud" based storage, etc.

As briefly described above, the protocol adherence module 136 determines whether a completed scan adhered to the scan protocol used to create the volume scan plan. For this, the protocol adherence module 136 performs an image analysis that identifies tissue, organs, landmarks, etc. in the field of view in volumetric image data. The protocol adherence module 136 then compares the identified tissue, organs, landmarks, etc. in the field of view with the tissue, organs, landmarks, etc. specified in the scan protocol used to create the scan plan. The protocol adherence module 136, based on the comparison, identifies deviations between the actual scan and the scan protocol and stores the deviations in storage such as the central storage of the imaging center, the RIS, the HIS, the "cloud" based storage, etc.

Figure 3:
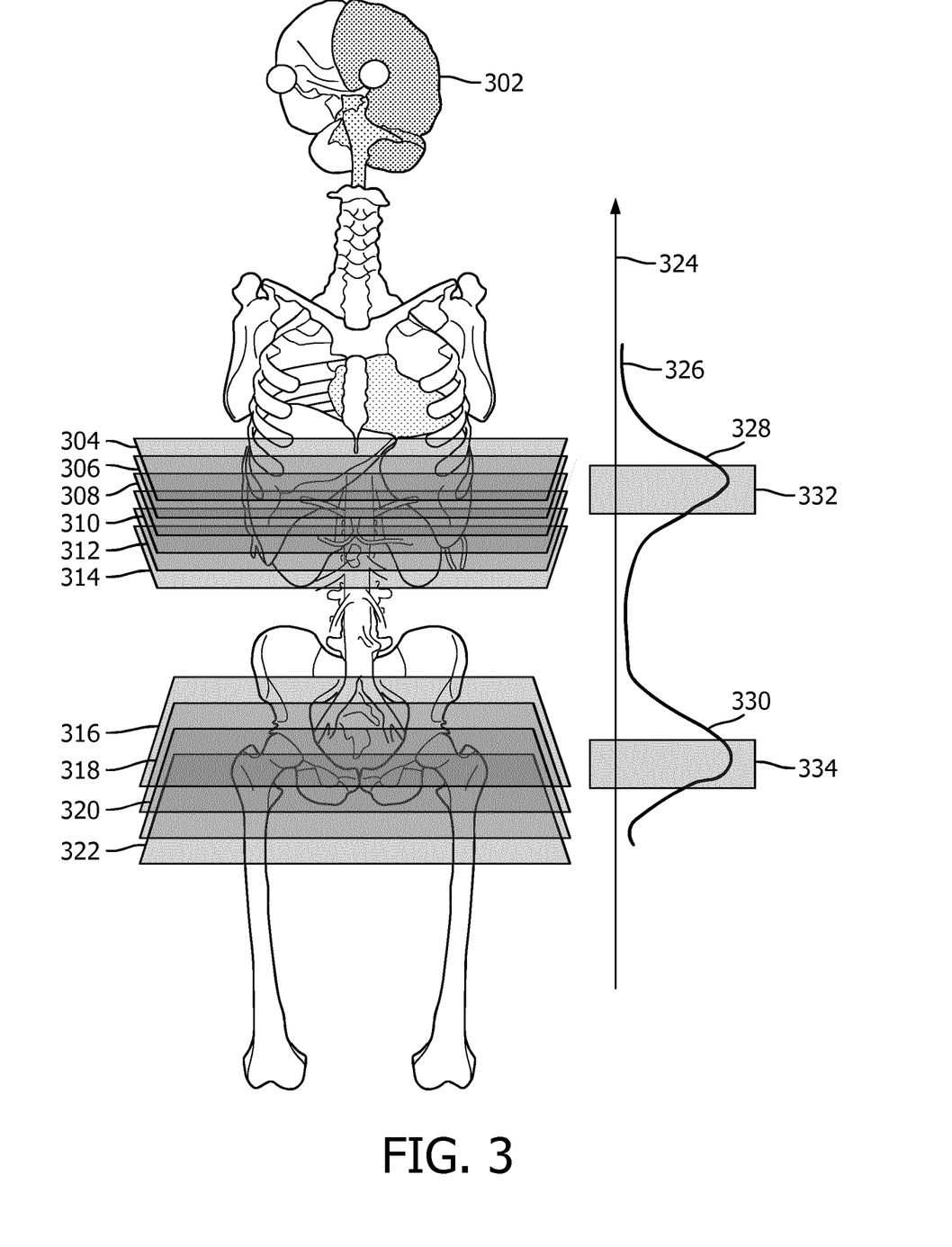
FIG. 3 schematically illustrates an example anatomical surface model with a line chart that shows deviations between actual field of views from scans and a field of view specified in the scan protocol.

FIG. 3 shows an example of the protocol adherence module 136 evaluating results from several different scans, all based on the same scan protocol. In one instance, the protocol adherence module 136 visually displays a copy 302 of the surface model 204 (FIG. 2) used to create the scan protocol with actual upper planes 304, 306, 308, 310, 312 and 314, and lower planes 316, 318, 320 and 322 for the several different scans that were based on the same scan protocol. Pairs of upper and lower planes define a scan field of view therebetween, as described in connection with the planes 206 and 208 and the scan field of view 205. The surface model 204 and planes 206 and 208 of FIG. 2 can be concurrently displayed with the copy 302 of the surface model 204.

In this example, a plot 324 shows a distribution 326 of the field of view deviation between the actual upper planes 304, 306, 308, 310, 312 and 314, and the lower planes 316, 318, 320 and 322 along a longitudinal axis of the subject. The distribution 326 includes a peak 332 about the (abdomen) for upper planes 304, 306, 308, 310, 312 and 314, and a peak 334 about the (pelvic) for the lower planes 316, 318, 320 and 322. Graphical representations 332 and 334 of the planes 206 and 208 of FIG. 2 are superimposed over the distribution 326. Alternatively, the actual upper and lower planes 304, 306, 308, 310, 312, 314, 316, 318, 320 and 322 can be compared with the planes 206 and 208 in FIG. 2. Generally, the narrower the peak, the greater the actual scans adhered to the scan protocol, and the broader the peak, the greater the actual scans did not adhere to the scan protocol. Again, breathing is one example that may cause a scan plan to shift from the desired location defined in the scan protocol to another position. Whether a field of view deviation of a particular scan is within an acceptable range depends on the particular type of scan, as different types of scan (e.g., abdomen vs pelvis) may have different tolerances. In addition, a same type of scan for different subjects may have different margins added to the field of view. As such, the scan protocol along with other information is used to determine acceptable ranges for the subject.

In one instance, the displayed upper and lower planes 304, 306, 308, 310, 312, 314, 316, 318, 320 and 322 are color-coded to visually indicate whether they adhere to the scan protocol. For example, in one instance the planes with field of views within the acceptable range are colored green, the planes with field of views outside of the acceptable range within a predetermined tolerance are colored yellow, and the planes with field of views outside of the predetermined tolerance are colored red. Other, different and/or more indicia can be used to visually indicate the adherence of the field of views of the upper and lower planes 304, 306, 308, 310, 312, 314, 316, 318, 320 and 322 with the scan protocol. In one instance, a plane colored red indicates the scan is insufficient and needs to be performed again with an adjusted plane.

Figure 4:
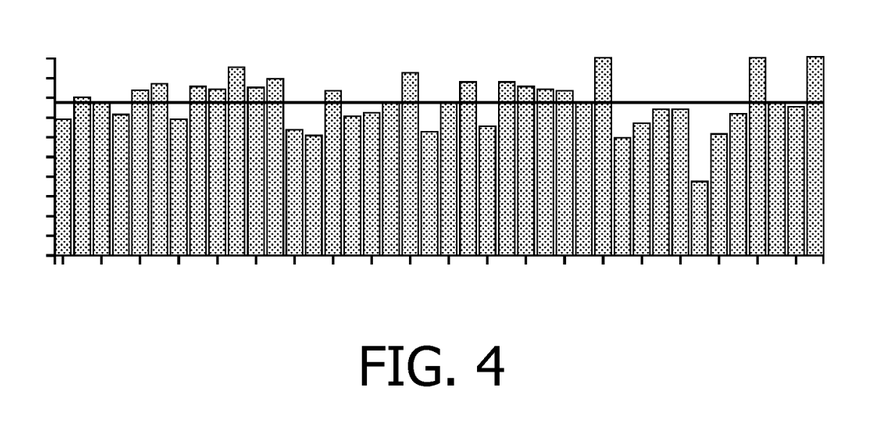
FIG. 4 shows a graph for one aspect (e.g., field of view, inhalation, rotation, etc.) of adherence to the scan protocol.

FIG. 4 shows a graph for one aspect (e.g., field of view, inhalation, rotation, etc.) of adherence to the scan protocol. The information is aggregated over a large number of scans. Each bar represents exams performed by one specific operator. A height of a bar indicates the percentage of protocol-adherent cases performed by this operator.

The embodiments shown in FIGS. 3 and 4 and/or other embodiments can be shown in a dashboard or the like in a graphical user interface and/or web interface of a display monitor of the output device 122 to indicate deviations from intended scan protocol for different technologists. In another instance, FIG. 3 is not visually presented, but the description above is utilized to determine the deviations. These statistics can be performed on demand, based on a schedule (e.g., monthly), etc., for all or a sub-set of scanned subjects, for all or a sub-sets of scan protocols, etc.

In one instance, the deviations are used to facilitate determining whether a scan complies with a scan plan. For example, movement, e.g., due to breathing, may cause tissue specified in the scan protocol to be included in the scan to move outside of the field of view where it was not scanned. In this instance, the deviation may indicate the scan does not comply with the scan protocol, and the protocol adherence module 136 may recommend repeating the scan. The recommendation is visually presented in the dashboard and/or otherwise conveyed to a user. In another example, movement, e.g., due to breathing, may cause tissue specified in the scan protocol to be excluded from the scan to move inside of the field of view where it is scanned. Likewise, the deviation may indicate the scan does not comply with the scan protocol, and the protocol adherence module 136 may recommend repeating the scan. In both examples, the scan may or may not actually be repeated.

The deviation determined by the protocol adherence module 136 is not limited to the above examples associated with repeating scans. For example, the deviation can additionally or alternatively be used to improve repeatability/efficiency. In this case, information indicating repeatability can be visually presented in the dashboard and/or otherwise conveyed to a user. Examples include, but are not limited to, the number and/or percentage of procedures where the scan satisfied the scan protocol the first time and the scan was not repeated; the number and/or percentage of procedures where the scan did not satisfy the scan protocol and the scan was repeated; the number of times a scan had to be repeated before the scan satisfied the scan protocol; and, the number of times a scan protocol failed to be repeated, etc.

Another example includes using the deviation for training. In this example, information can be visually presented in the dashboard and/or otherwise conveyed to a user to instruct the trainee and/or provide feedback to the trainee. The information may indicate a suggestion to assist the trainee with performing a scan that complies with the scan protocol, the number of times the trainee successfully completed a scan that complied with the scan protocol on the first try, the number of times the trainee had to repeat a scan before the scan complied with the scan protocol, etc. Other examples include using the deviation to improve data correlation, e.g., in clinical studies, to establish a uniformity in practice, e.g., to establish whether a study is reimbursed, etc.

Again, although the above is described in detail with respect to CT, it also applies to other imaging modalities such as MRI, etc. For instance, with MRI, the information region 210 can include specifying an MR sequence, an orientation, a particular coil, etc.

Figure 5:
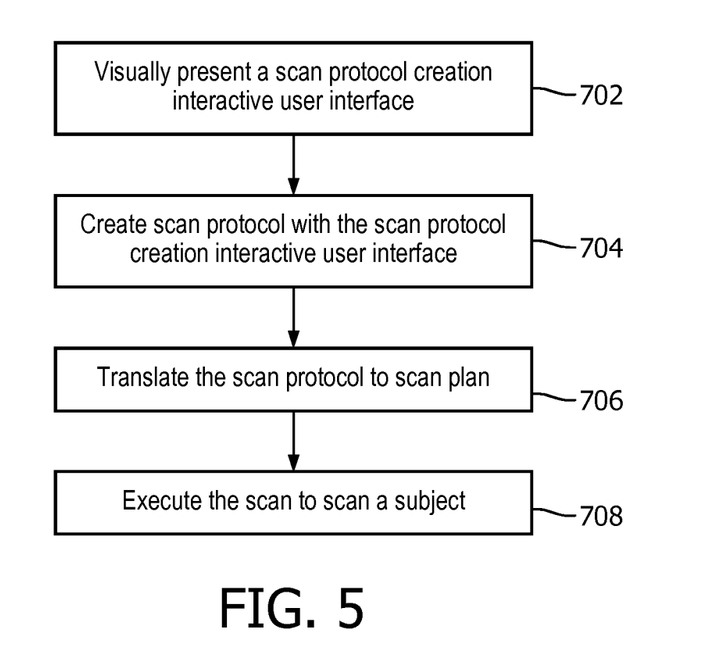
FIG. 5 illustrates an example method in accordance with an embodiment(s) herein.

FIG. 5 illustrates an example method in accordance with an embodiment(s) herein.

At 502, a scan protocol creation interactive user interface (e.g., the interactive user interface 202) is visually presented, as described herein and/or otherwise.

At 504, a user creates a scan protocol, including a field of view(s), using the scan protocol creation interactive user interface, as described herein and/or otherwise.

At 506, the scan protocol, including the field of view(s), is translated to a scan plan, as described herein and/or otherwise.

At 508, the scan plan is executed by the imaging system 100, as described herein and/or otherwise.

For example, breathing may cause organs and/or landmarks to move out of the field of view during scanning. In this instance, deviations showing the organs and/or landmarks are consistently not in the image data, even though the organs and/or landmarks are within the field of view in the scan plan, may result in an increase in the size of the field of view in the scan protocol to compensate for motion due to breathing.

Additionally, or alternatively, this may result in repeating the scan to generate image data for the subject that includes these organs and/or landmarks. In another instance, a deviation showing that organs and/or landmarks identified in the scan protocol as being excluded are in the image data may result in decreasing the field of view so that these organs and/or landmarks are not present in the image data. This may reduce patient dose.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus, comprising:
a memory configured to store a protocol definition module;
a display; and
a processor configured to:
execute the protocol definition module, which causes the processor to display, via the display, an interactive graphical tool that includes a digital representation of an anatomical model with an interactively generated scan field of view superimposed thereover to create a scan protocol for execution by an imaging system, wherein the scan field of view identifies anatomy of a subject to scan for the scan protocol;
selects the digital representation to display from a collection of digital representations including at least a first digital representation specific to first anatomy and a second different digital representation specific to second different anatomy, wherein the selected digital representation includes the anatomy of interest;
display an information region in the interactive graphical tool, the information region populated with at least one of an offset, a width, an angularization, a slice thickness, and an image resolution, landmark, or organ to be included or excluded, an external device being used for the scan, CT dose, or other scan specifier;
translate the scan protocol, including the scan field of view, to a pre-scan projection image of a scan plan;
analyze volumetric image data generated by the imaging system to determine whether the volumetric image data adheres to the scan protocol; and
display deviations between the volumetric image data and the scan protocol.

2. The apparatus of claim 1, wherein the digital representation further includes a surface model or an anatomical atlas.

3. The apparatus of claim 1, wherein the processor creates the scan field of view with at least two planes, each having an orientation and different position over the anatomical model.

4. The apparatus of claim 1, wherein the processor positions the scan field of view over the digital representation at a location of the anatomy of interest.

5. The apparatus of claim 1, wherein the processor changes a geometry or a location of the scan field of view in response to a geometry or a location change indicated by the input device.

6. The apparatus of claim 1, wherein the processor changes the information in the information region in response to an information change indicated by an input device.

7. A non-transitory computer readable medium storing instructions that, when executed by one or more processors, cause the one or more processors to:
display, via a display, an interactive graphical tool that includes a digital representation of an anatomical model with an interactively generated scan field of view superimposed thereover to create a scan protocol for execution by an imaging system, wherein the scan field of view identifies anatomy of a subject to scan for the scan protocol and the digital representation includes a surface model or an anatomical atlas;
select the digital representation to display from a collection of digital representations;
pre-populate the digital representation with the scan field of view, which is predetermined;
position the scan field of view over the digital representation at a location of the anatomy of interest;
receive a signal as input, and the signal indicates anatomy of interest, and select, based on the anatomy of interest, the digital representation to display from a collection of digital representations, which includes at least a first digital representation specific to first anatomy and a second different digital representation specific to second different anatomy, and selected digital representation includes the anatomy of interest; and
analyze volumetric image data generated by the imaging system to determine whether the volumetric image data adheres to the scan protocol.

8. The non-transitory computer readable medium claim 7, storing further instructions to create the scan field of view with at least two planes, each having an orientation and different position over the anatomical model.

9. The non-transitory computer readable medium claim 7, storing further instructions to change a geometry or a location of the scan field of view in response to a geometry or a location change indicated by the input device.

10. The non-transitory computer readable medium claim 7, storing further instructions to further display an information region in the interactive graphical tool, and populates the information region with at least one of an offset, a width, an angularization, a slice thickness, and an image resolution, landmark or organ to be included or excluded, an external device being used for the scan, CT dose, or other scan specifier.

11. The non-transitory computer readable medium claim 10, storing further instructions to change the information in the information region in response to an information change indicated by an input device.

12. The non-transitory computer readable medium claim 7, storing further instructions to store a scan plan module, and execute the scan plan module, wherein executing the scan plan module includes translating the scan protocol, including the scan field of view, to a pre-scan projection image of a scan plan.

13. The non-transitory computer readable medium claim 7, storing further instructions to display deviations between the volumetric image data and the scan protocol in a dashboard visually presented via the display.

14. A computer-implemented method for performing a scan protocol, the method comprising:
displaying an interactive graphical tool that includes a digital representation of an anatomical model with an interactively generated scan field of view superimposed thereover to create a scan protocol for execution by an imaging system, wherein the scan field of view identifies anatomy of a subject to scan for the scan protocol;

receiving an indication of anatomy of interest;

selecting the digital representation to display from a collection of digital representations including at least a first digital representation specific to first anatomy and a second different digital representation specific to second different anatomy, wherein the selected digital representation includes the anatomy of interest;

displaying an information region in the interactive graphical tool, the information region populated with at least one of an offset, a width, an angularization, a slice thickness, and an image resolution, landmark or organ to be included and/or excluded, an external device being used for the scan, CT dose, or other scan specifier;

translating the scan protocol, including the scan field of view, to a pre-scan projection image of a scan plan;

analyzing volumetric image data generated by the imaging system to determine whether the volumetric image data adheres to the scan protocol; and displaying deviations between the volumetric image data and the scan protocol.

* * * * *